(12) United States Patent
Zhao et al.

(10) Patent No.: US 11,987,567 B2
(45) Date of Patent: May 21, 2024

(54) SYNTHESIS METHOD OF LACTIDE BY CONFINEMENT EFFECT CATALYSIS OF CRYSTALLINE POROUS POLYMER MATERIAL

(71) Applicant: Qingdao University of Science and Technology, Shandong (CN)

(72) Inventors: Yingjie Zhao, Shandong (CN); Wenqi Qiu, Shandong (CN); Hui Liu, Shandong (CN); Zhenxiu Zhang, Shandong (CN); Jinyu Zhao, Shandong (CN)

(73) Assignee: QINGDAO UNIVERSITY OF SCIENCE AND TECHNOLOGY, Shandong (CN)

( * ) Notice: Subject to any disclaimer, the term of this patent is extended or adjusted under 35 U.S.C. 154(b) by 0 days.

(21) Appl. No.: 17/899,814

(22) Filed: Aug. 31, 2022

(65) Prior Publication Data
US 2023/0094928 A1   Mar. 30, 2023

(30) Foreign Application Priority Data

Sep. 15, 2021  (CN) .......................... 202111078761.5

(51) Int. Cl.
| | | |
|---|---|---|
| *C07D 319/12* | (2006.01) | |
| *B01J 31/04* | (2006.01) | |
| *B01J 37/00* | (2006.01) | |
| *B01J 37/02* | (2006.01) | |
| *B01J 37/03* | (2006.01) | |
| *B01J 37/04* | (2006.01) | |
| *B01J 37/06* | (2006.01) | |

(52) U.S. Cl.
CPC ............ *C07D 319/12* (2013.01); *B01J 31/04* (2013.01); *B01J 37/009* (2013.01); *B01J 37/0236* (2013.01); *B01J 37/031* (2013.01); *B01J 37/04* (2013.01); *B01J 37/06* (2013.01); *B01J 2231/005* (2013.01); *B01J 2531/002* (2013.01)

(58) Field of Classification Search
CPC ....... C07D 319/12; B01J 31/04; B01J 37/009; B01J 37/0236; B01J 37/031; B01J 37/04; B01J 37/06; B01J 2231/005; B01J 2531/002
See application file for complete search history.

(56) References Cited

PUBLICATIONS

Wang et al., Green Chem., 2020, 22, 2605-2612 (Year: 2020).*
Verpoort et al., Catalysis Communications 114 (2018) 33-36 (Year: 2018).*
Jiang et al., Chem. Rev. 2020, 120, 8814-8933 (Year: 2020).*
Zhang et al., Small 2020, 16, 2001070 (Year: 2020).*
Yu et al., Chem. Mater. 2020, 32, 751-758 (Year: 2020).*
Xu, Wang et al., Journal of Membrane Science 611 (2020) 118297 (Year: 2020).*

* cited by examiner

*Primary Examiner* — Andrew D Kosar
*Assistant Examiner* — John D McAnany
(74) *Attorney, Agent, or Firm* — McClure, Qualey & Rodack, LLP

(57) ABSTRACT

The present invention discloses a synthesis method of lactide by confinement effect catalysis of crystalline porous polymer material, wherein the method comprising: (I) synthesis of catalyst; (II) synthesis of lactide by confinement effect catalysis; and (III) purification of lactide. In the present invention, a yield of L-lactide by catalysis of L-lactic acid by crystalline polymers is as high as 85.6%, which is 10% higher than the yield of lactide by H-β molecular sieve reported in documents currently available; it is easy to prepare the crystalline porous polymer material catalyst, which is environmental friendly, has a high yield and is recyclable, for consecutive 7 times the catalysis yield is maintained to be higher than 70%, and catalysis yield conservation rate is far higher than catalysis effects of catalysts reported in documents currently available.

2 Claims, 5 Drawing Sheets

SYNTHESIS METHOD OF LACTIDE BY CONFINEMENT EFFECT CATALYSIS OF CRYSTALLINE POROUS POLYMER MATERIAL

TECHNICAL FIELD

The present invention belongs to the technical field of lactide preparation processes, and in particular a synthesis method of lactide by confinement effect catalysis of crystalline porous polymer material.

BACKGROUND TECHNOLOGY

Poly-lactic acid (PLA) is a main kind of synthesized bio-based plastic commercially available, and the application field thereof is very wide. PLA products can replace fossil-based plastic products currently available, and wastes thereof can be biodegraded completely in a short term; therefore, PLA products are judged to be of good environmental properties during life cycle assessment.

The monomers used to synthesize PLA comprise lactic acid and lactide, wherein lactide is a cyclic dimer of lactic acid, chemical ways to synthesize the PLA comprise ring-opening polymerization of lactide (also called two-step process) and direct polycondensation of lactic acid, wherein the two-step process involves the following processes: lactic acid, catalyst→atmospheric distillation→vacuum distillation→coarse lactide→lactide purification→ring opening and polymerization→post treatment→PLA product, by the two-step process PLA products of higher relative molecular weights can be obtained, however, increase of reaction steps makes the process more complex than one-step process and the intermediate product lactide is liable to absorb water.

Currently in the industry the two-step process is adopted for preparing lactide, first of all, dehydrate the lactic acid and lactic acid oligomers are formed, catalyze and degrade the oligomers at high temperature and obtain the lactide, for production of lactide, metal salts are used as catalysts, wherein metal salts comprise mainly composites of zinc or tin. The entire preparation process shall be done at conditions of high temperature, negative pressure and catalysis, in the meanwhile, to improve overall yield, unreacted matters shall be refluxed and used repeatedly, finally qualified lactide products can be obtained by some purification methods. Lactide production processes comprise primarily several units such as condensation, decomposition, cyclization and purification. Metal salts, which comprise composites of zinc and tin, are mainly used as catalysts in lactide production.

Conventionally the two-step process for preparing lactide in the industry has a low yield, a large quantity of oligomers are generated, there are many factors that may influence preparation thereof, it is difficult to purify the oligomers, and as a result the cost is high. The metal catalysts used are liable to pollute the product and the environment, which runs against environment protection and the yield rate is low.

Currently for lactide production processes metal catalysts are used, the metal catalysts being composites of zinc and tin, for example zinc oxide, stannous octoate and stannous chloride, a research team from Nanjing University discovered that organic guanidine catalysts and alkali metal catalysts can also be used in production of lactide and lactic acid. However, the catalysts used now have the following problems:

(1) As some catalysts are powdered solids, it is difficult for them to dissolve and react fully with lactic acid and it is also difficult to introduce a vacuum system and the yield of lactide is finally influenced;
(2) The metal catalysts are liable to remain in the lactide, which runs against the concept of green technology and environmental protection, and the metal residue shall be controlled strictly;
(3) Organic guanidine catalysts don't contain metal elements and are green catalysts with very good developing prospects, however, this kind of catalyst has not been used across the world, chemical properties and economic performance thereof shall be further verified in engineering scaling-up experiments.

Lactide is a key to the preparation of PLA through the two-step process, and the purity of the lactide decides the molecular weight and usage values of the PLA after ring-opening polymerization of lactide. Conventional ways to purify the lactide are primarily recrystallization. Lactide for use in making polymers of relatively high molecular masses such as surgical sutures shall be recrystallized four times, while a primary recovery rate of lactide is only 93.1%, furthermore, a large number of solvents are wasted during purification processes, it is difficult to recover the solvents, which increases expenses and constitutes a primary reason why the cost of indirect polymerization is high.

SUMMARY OF INVENTION

The present invention is proposed to address the deficiencies of the prior technique, and aims to provide a synthesis method of lactide by confinement effect catalysis of crystalline porous polymer material.

The present invention is realized by the following technical solutions:

A synthesis method of lactide by confinement effect catalysis of crystalline porous polymer material, comprising the following steps:

(I) Synthesis of Catalysts

Putting a compound A, a compound B, mesitylene and 1,4-dioxane into a reaction vessel, mixing evenly, adding acetic acid, de-aerating, vacuum sealing, putting into a drying oven for drying, filtering precipitates, washing with a Soxhlet extractor, vacuum drying and solid catalysts are obtained;

Wherein a structural formula of the compound A is:

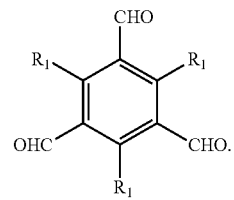

Wherein $R_1$=OH, $CH_3$, $OCH_3$, $C_2H_5$, F, Cl, Br or I;
Wherein a structural formula of the compound B is:

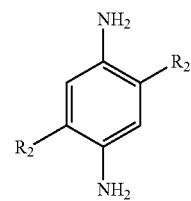

Wherein R₂=COOH, CH₃, OCH₃, C₂H₅, F, Cl, Br or I;

(II) Confinement Effect Catalysis for Synthesis of Lactide

Adding the catalysts obtained in step (I), solvents, and lactic acid to a reaction vessel for reaction, cooling down slowly after reaction, filtering, washing, removing the solvents at low pressure and coarse lactide is obtained; and (III) Lactide Purification Conducting liquid-liquid treatment to the coarse lactide obtained in step (II) with methylbenzene and water, taking organic phases, removing the solvents at low pressure, L-lactide is obtained.

In the foregoing technical solution, the structural formula of the compound A is

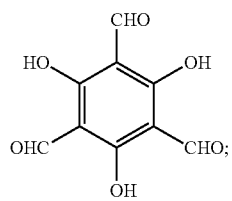 [SMILES: O=Cc1c(O)c(C=O)c(O)c(C=O)c1O]

and the structural formula of the compound B is

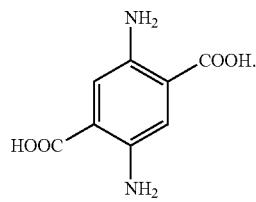

In the foregoing technical solution, in step (I) a mole ratio between the compound A and the compound B is 4:7; a volume ratio among the mesitylene, the 1,4-dioxane and the acetic acid is 15:5:1; and a mole ratio between the compound A and the mesitylene is 1:25.

In the foregoing technical solution, in step (I) a method for de-aerating comprises freeze-pump-thaw cycling.

In the foregoing technical solution, in step (I) conditions for drying the drying oven comprise 80° C. and 3 days; washing with the Soxhlet extractor comprises specifically: washing respectively 4 hours with tetrahydrofuran (THF) and acetone; and conditions for vacuum drying comprise: 80° C. and 12 hours.

In the foregoing technical solution, lactic acid in step (II) comprises L-lactic acid 90 wt %.

In the foregoing technical solution, the solvents in step (II) comprise methylbenzene or ortho-xylene.

In the foregoing technical solution, a mass ratio between the catalysts and the lactic acid is 1:10, and a weight/volume ratio of the catalysts and the solvents is 1:1.

In the foregoing technical solution, reaction conditions in step (II) comprise: reaction time 5 h and reaction temperature 120° C.

In the foregoing technical solution, in step (II) washing is done by washing with acetonitrile.

Beneficial Effects of the Present Invention

In the present invention, a synthesis method of lactide by confinement effect catalysis of crystalline porous polymer materials is disclosed, wherein the crystalline polymers catalyze L-lactic acid and synthesize L-lactide with a yield rate as high as 85.6%, which is 10% higher than the yield when catalyzing with an H-β molecular sieve; and it is easy to prepare the crystalline porous polymer catalyst, which is environmental friendly, has a high yield and is recyclable, for consecutive 7 times the catalysis yield is maintained at over 70%, and the catalysis conservation degree is far higher than catalysis effects by catalysts reported in documents currently available.

EMBODIMENTS

Figure 1:
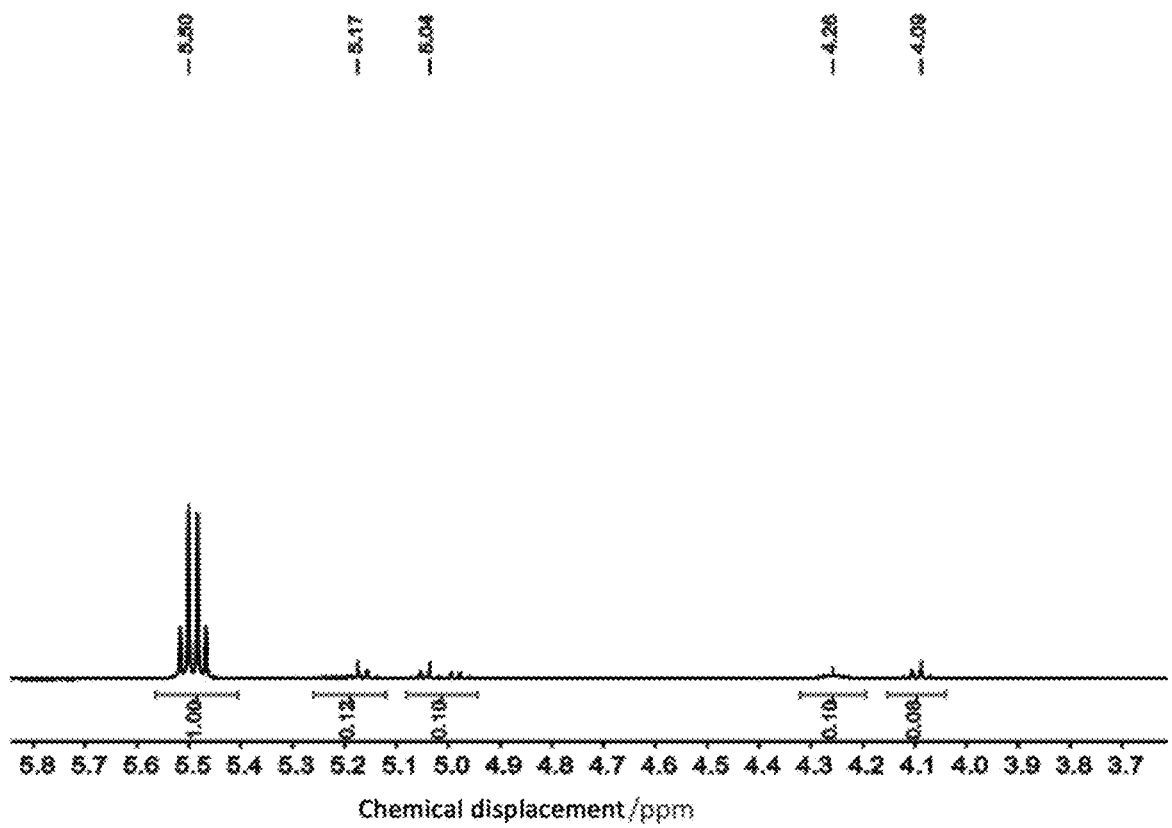
FIG. 1 shows ¹H NMR data after catalysis reaction of the catalyst in embodiment 1 of the present invention.
Figure 2:
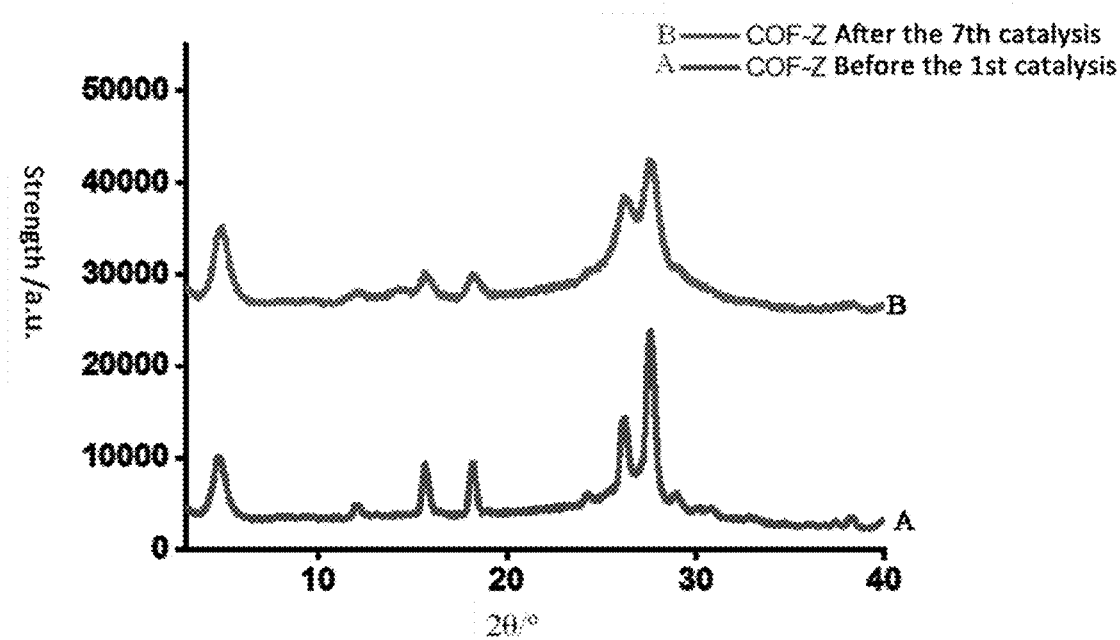
FIG. 2 is an XRD data diagram showing the catalyst going through repeated tests in the present invention (A is before the first catalysis reaction, and B is after the seventh catalysis reaction experiment)
Figure 3:
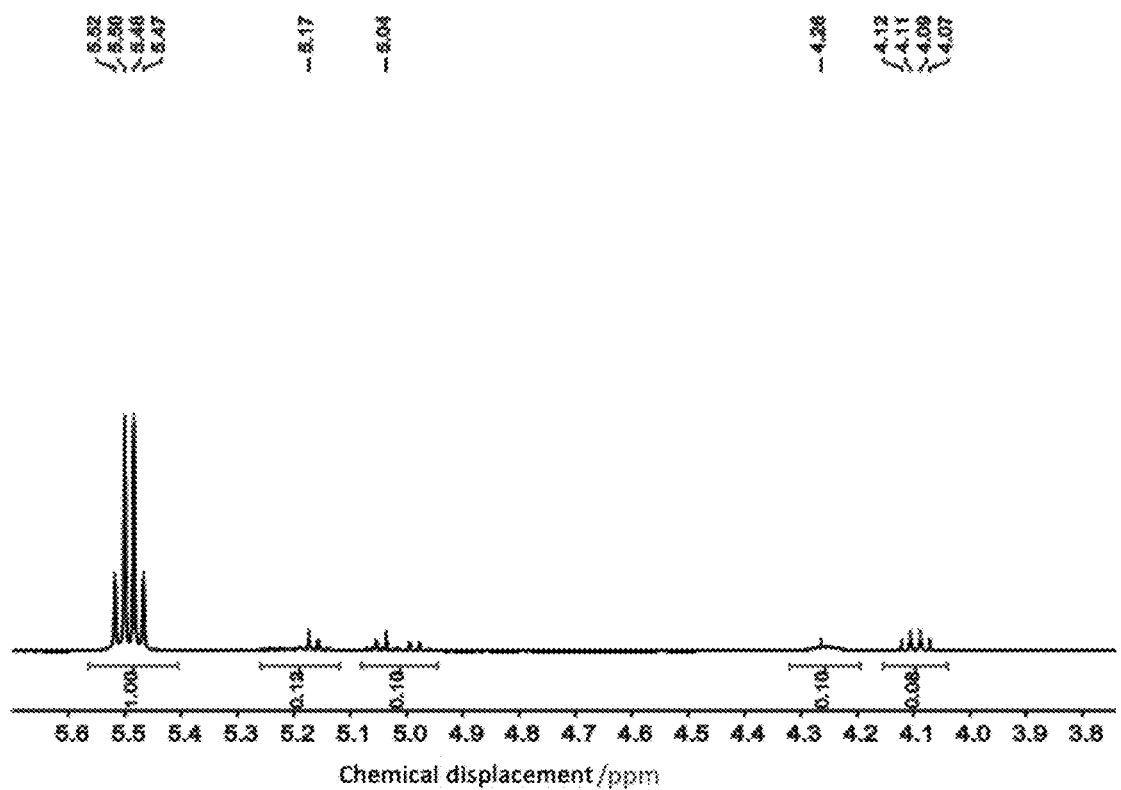
FIG. 3 shows ¹H NMR data of the catalyst after the first catalysis experiment among the repeated tests in the present invention.
Figure 4:
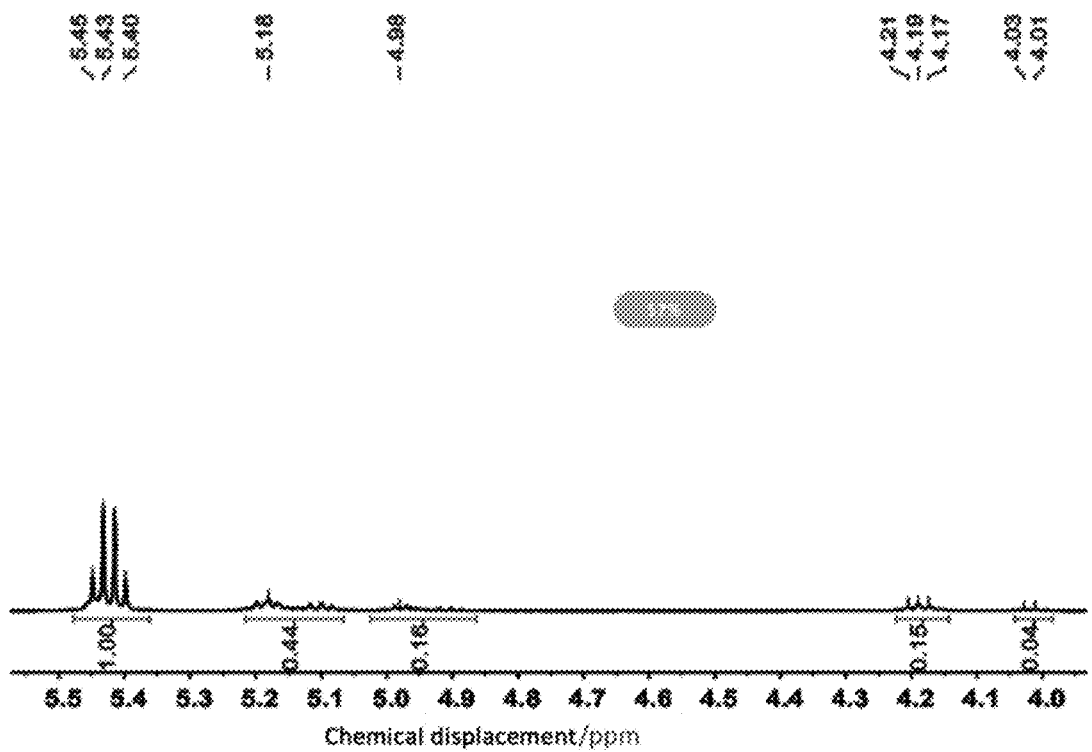
FIG. 4 shows ¹H NMR data of the catalyst after the second catalysis experiment among the repeated tests in the present invention.
Figure 5:
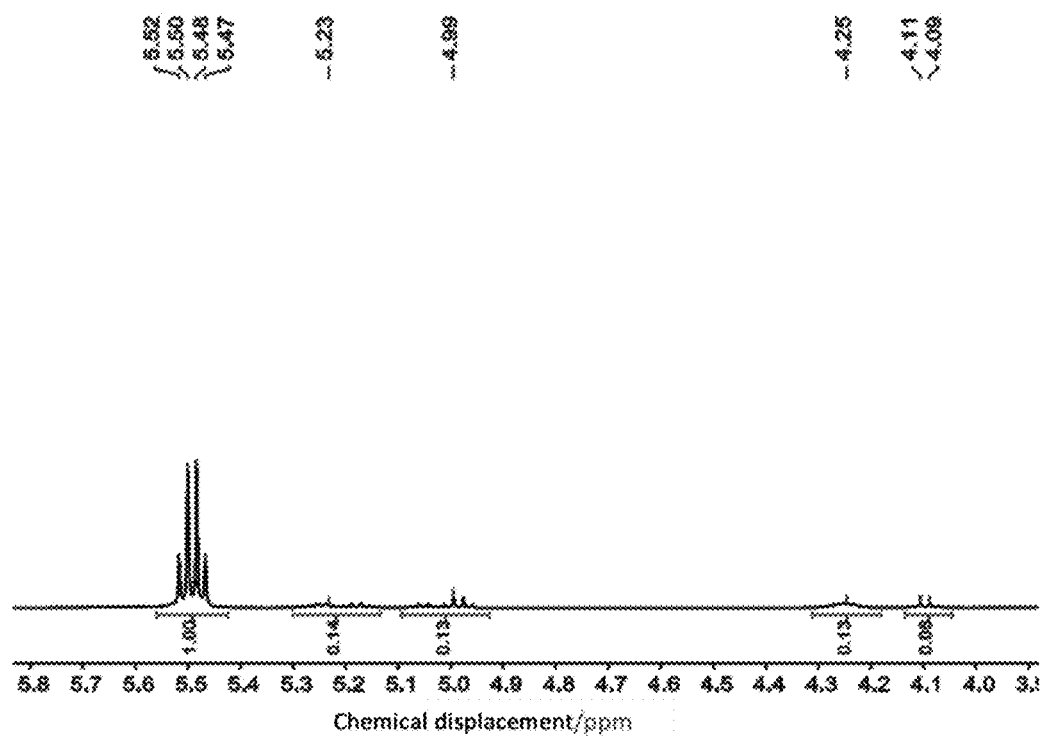
FIG. 5 shows ¹H NMR data of the catalyst after the third catalysis experiment among the repeated tests in the present invention.
Figure 6:
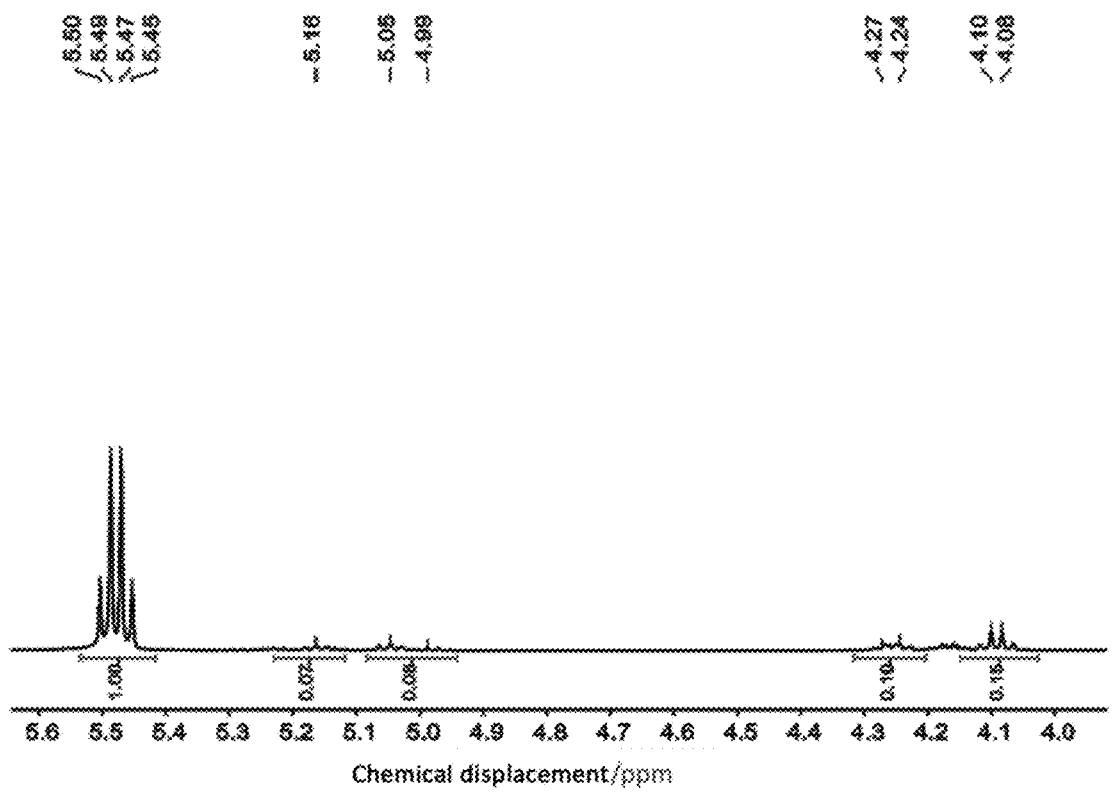
FIG. 6 shows ¹H NMR data of the catalyst after the fourth catalysis experiment among the repeated tests in the present invention.
Figure 7:
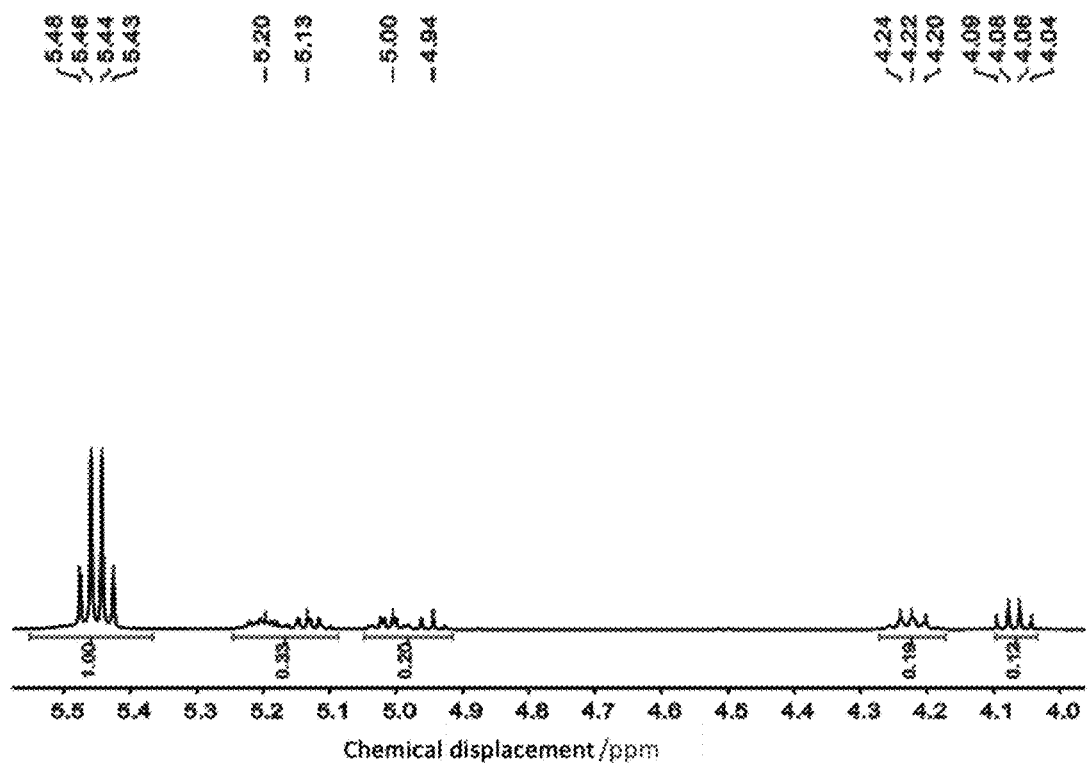
FIG. 7 shows ¹H NMR data of the catalyst after the fifth catalysis experiment among the repeated tests in the present invention.
Figure 8:
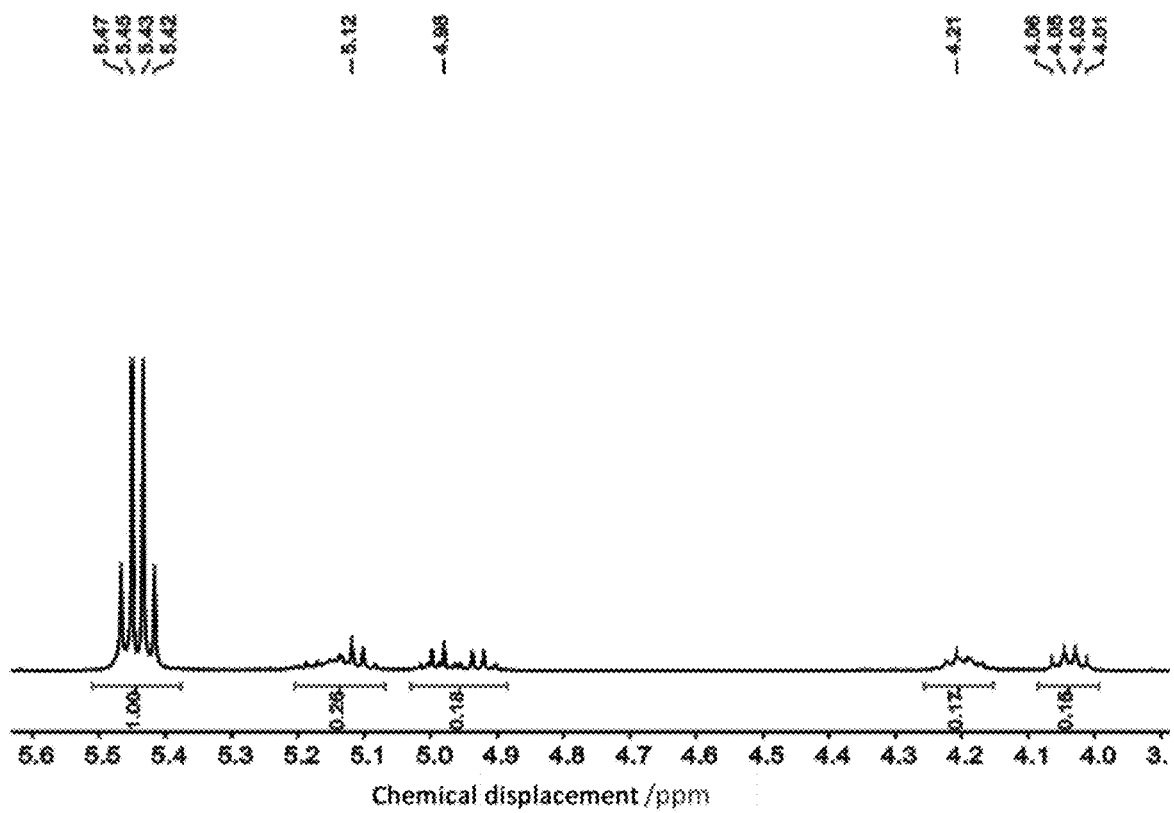
FIG. 8 shows ¹H NMR data of the catalyst after the sixth catalysis experiment among the repeated tests in the present invention.
Figure 9:
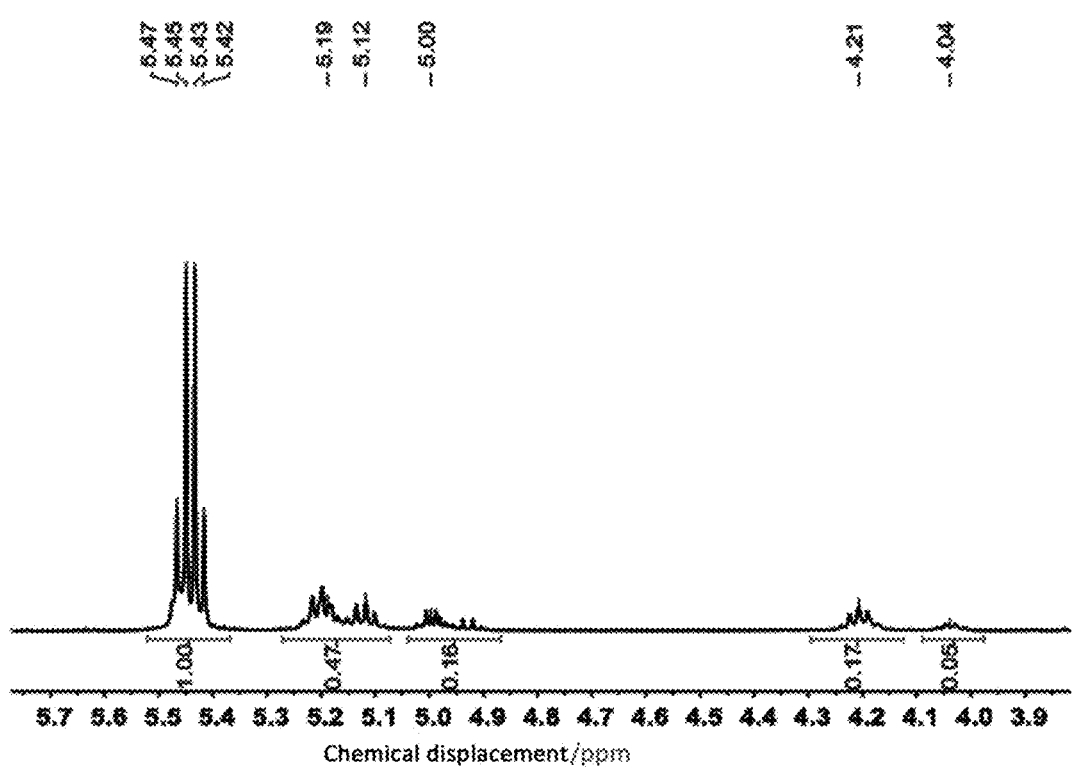
FIG. 9 shows ¹H NMR data of the catalyst after the seventh catalysis experiment among the repeated tests in the present invention.

To enable those of ordinary skill in the art to understand the technical solutions in the present invention more clearly, hereinafter the technical solutions of the present invention will be further described in conjunction with the accompanying drawings and the embodiments.

Embodiment 1

A synthesis method of lactide by confinement effect catalysis of crystalline porous polymer material, comprising the following steps:

(I) Catalyst Synthesis

Adding compound A 0.6 mmol and compound B 0.9 mmol in a heat-proof glass tube, adding mesitylene 4 ml and 1,4-dioxane 16 ml, mixing evenly by ultrasonic treatment, adding 3 M acetic acid 6 ml, de-aerating for three times by freeze-pump-thaw cycling, vacuum sealing, putting in a drying oven at 80° C. for three days, filtering precipitates, washing with a Soxhlet extractor by THF and acetone for respectively 4 hours, vacuum drying at 80° C. overnight, and solid catalysts COF-Z with a yield rate of 93% is obtained;

5
Wherein a structural formula of the compound A is
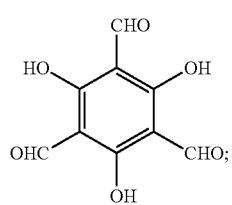 [SMILES: O=Cc1c(O)c(C=O)c(O)c(C=O)c1O]
6
A structural formula of the compound B is
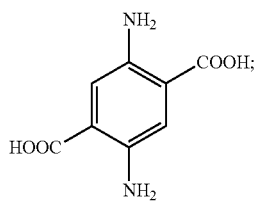
A reaction formula showing synthesis of the catalyst is:
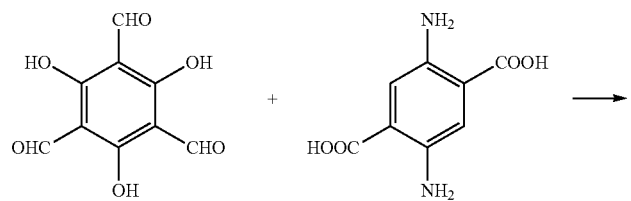
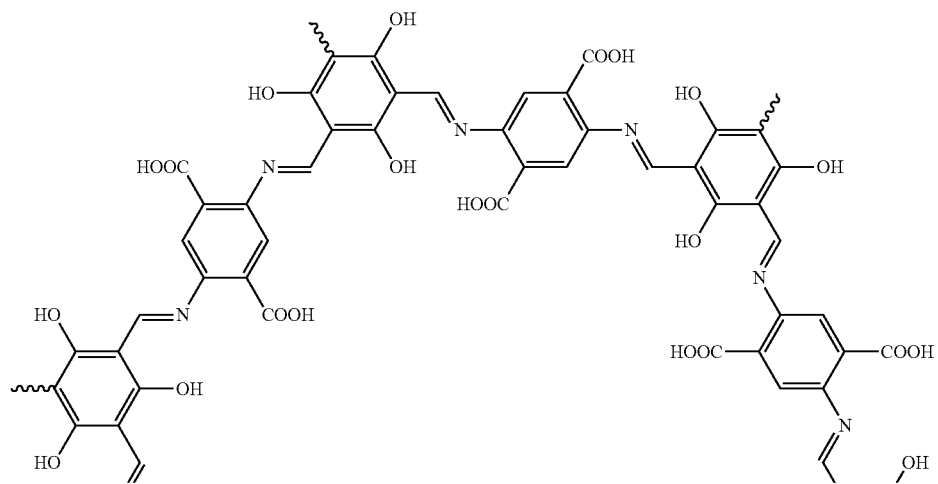
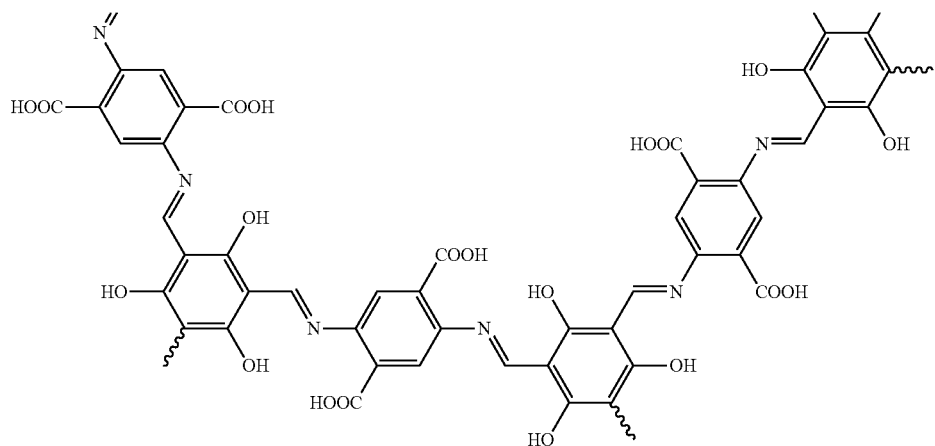

(II) Confinement Effect Catalysis for Synthesis of Lactide

Adding the catalyst COF-Z 10 mg obtained in step (I) in a round bottom flask 25 ml, 90 wt % L-LA 100 mg, mesitylene or ortho-xylene 10 ml, adding a water knockout vessel on the flask, connecting a condenser tube on the water knockout vessel, reacting for 5 h, cooling slowly, filtering, washing with acetonitrile, removing solvents at low pressure, calculating yield with HPLC and 1H-NMR, it is found that the yield after catalysis with COF-Z-1 is the highest, which is 85.6%. The nuclear-magnetism data after catalysis treatment by COF-Z-1 are shown in FIG. 1.

(III) Lactide Purification

After removing solvents at low pressure (it can be seen that obviously a lot of crystalloid is at a bottom portion of the flask), coarse lactide is obtained, conducting liquid liquid extraction with methylbenzene and water, taking organic phases, removing solvents therein and L-lactide with a purity of 98.5% is obtained.

Repeated Test

Repeated tests are done at the same conditions as those for embodiment 1. Experiment conditions of the repeated trials are the same as those for embodiment 1, the same catalyst is used in the repeated trials, catalysts recovered from last experiment are used, masses of L-lactic acid used in the present experiment are decided by masses of the catalysts recovered, wherein the mass of L-lactic acid shall be 10 times the mass of the catalyst, specifically, the data are shown in the following table.

| S. N. | Remaining mass of the catalyst (COF-Z) after loss in the previous reaction/mg | L-lactic acid/mg | Yield of lactide |
|---|---|---|---|
| 1 | 50 | 100 | 85.6 |
| 2 | 48.3 | 96.6 | 82.4 |
| 3 | 45.8 | 91.6 | 83.5 |
| 4 | 42.3 | 84.6 | 75.7 |
| 5 | 40.0 | 80 | 73.1 |
| 6 | 38.3 | 76.6 | 73.0 |
| 7 | 37.0 | 74 | 70.09 |

From the foregoing experimental data and FIGS. 2-9, it can be known that, the catalyst COF-Z-1 can have a yield of over 70% after catalysis of consecutive 7 times in ortho-xylene, and by XRD comparison, structure thereof is still complete, so the catalyst COF-Z-1 has high stability and reproducibility.

Reaction Principles of the Present Invention:

(I) Catalyst Synthesis

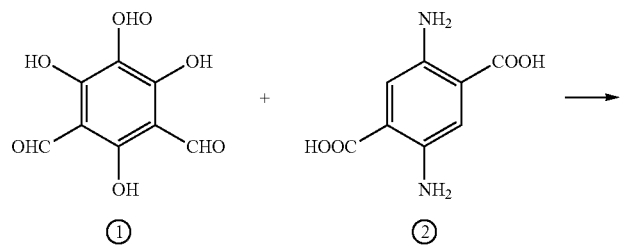

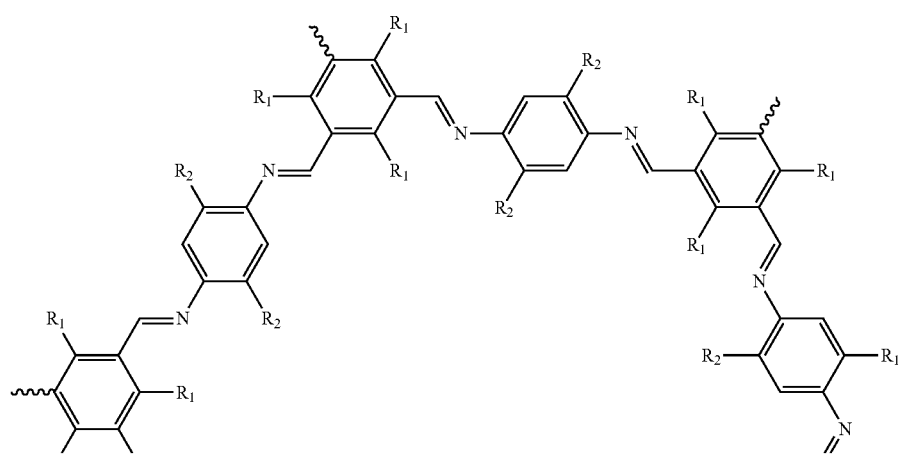

-continued
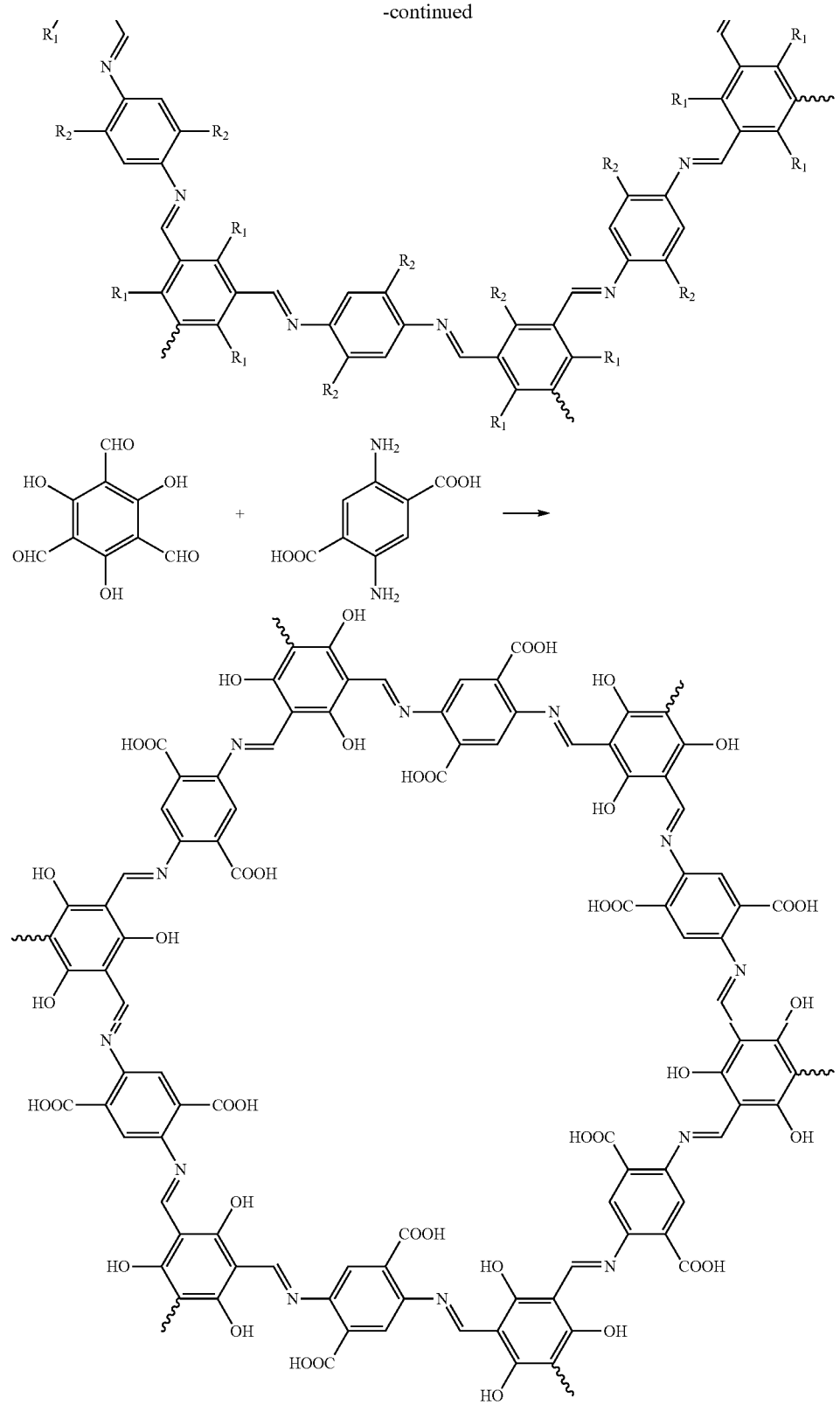
R₁ = OH, CH₃, OCH₃, C₂H₈, F, Cl, Br, I ...
R₂ = COOH, CH₃, OCH₃, C₂H₈, F, Cl, Br, I ...
As the catalyst COF-Z has a large number of carboxyl and hydroxyl functional groups, hydrogen ions can be ionized from methylbenzene and ortho-xylene, and pore diameters of COF-Z are around 2.1 nm, a length of L-lactic acid is around 0.4 nm, COF-Z can make shape-selective catalysis and the ionized hydrogen ions promote cyclization of the dimers to form the lactide.

The applicant declares that, the foregoing are only some specific embodiments of the present invention, the protection scope of the present invention is not limited to these embodiments disclosed here, those skilled in the art shall appreciate that, any change or replacement that one of ordinary skill in the art can easily come up with within the technical scope disclosed in the present invention falls into the protection scope of the present invention.

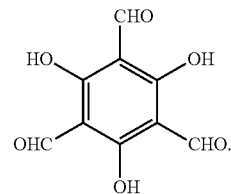

The invention claimed is:

1. A synthesis method of lactide by confinement effect catalysis of crystalline porous polymer material, comprising following steps:
   step (I) synthesis of catalysts comprising:
   a) placing a compound A, a compound B, mesitylene and 1,4-dioxane into a reaction vessel;
   b) mixing the contents of the reaction vessel evenly;
   c) adding acetic acid to the reaction vessel;
   d) de-aerating the contents of the reaction vessel;
   e) vacuum sealing the reaction vessel;
   f) placing the reaction vessel in an oven for heating;
   g) filtering precipitates from the reaction vessel;
   h) washing the precipitates with a Soxhlet extractor;
   i) vacuum drying the precipitates; and
   j) obtaining solid catalysts;
   wherein a structural formula of the compound A is:

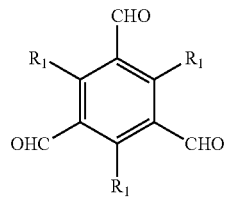

wherein $R_1$ =OH, $CH_3$, $OCH_3$, $C_2H_5$, F, Cl, Br or I;
wherein compound B is:

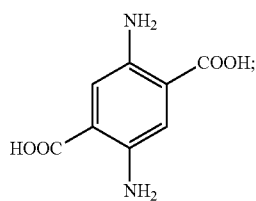 [SMILES: Nc1cc(C(=O)O)c(N)cc1C(=O)O]

step (II) synthesis of lactide by confinement effect catalysis comprising:
a) adding the catalysts obtained in step (I), solvents, and lactic acid to a reaction vessel for reaction;
b) cooling down the reaction vessel slowly after the reaction;
c) filtering the contents of the reaction vessel after the reaction;
d) washing the contents of the reaction vessel after the reaction;
e) removing the solvents from the contents of the reaction vessel after the reaction at low pressure; and
f) obtaining crude lactide;
step (III) lactide purification comprising:
a) conducting liquid-liquid extraction on the crude lactide obtained in step (II) with methylbenzene and water,
b) combining organic phases of the liquid-liquid extraction,
c) removing the solvents of the combined organic phases at low pressure, and
d) obtaining lactide,
wherein in step (I) a mole ratio between the compound A and the compound B is 4:7; a volume ratio among the mesitylene, the 1,4-dioxane, and the acetic acid is 15:5:1; and a mole ratio between the compound A and the mesitylene is 1:25;
wherein in step (I) the method for de-aerating comprises freeze-pump-thaw cycling;
wherein in step (I) the conditions for heating in the oven comprise 80° C. for 3 days;
wherein in step (I) the conditions for washing with the Soxhlet extractor comprise specifically: washing four hours with THF and acetone; and conditions for vacuum drying comprise: 80° C. for 12 hours;
wherein lactic acid in step (II) comprises L-lactic acid of 90 percent purity;
wherein the solvents in step (II) comprise methylbenzene or ortho-xylene; wherein a mass ratio between the catalysts and the lactic acid is 1:10, and a weight/volume ratio of the catalysts and the solvents is 1:1 $g/cm^3$;
wherein reaction conditions in step (II) comprise: reaction time of 5 hr and reaction temperature 120° C.;
wherein in step (II) washing is done by washing with acetonitrile.

2. The synthesis method of lactide by confinement effect catalysis of crystalline porous polymer material according to claim 1, wherein the structural formula of the compound A is